Patent …

[54] METHOD FOR MEASURING FASTENER STRESS UTILIZING LONGITUDINAL AND TRANSVERSE ULTRASONIC WAVE TIME-OF-FLIGHT

[75] Inventor: Albert C. Holt, Trinidad, Calif.

[73] Assignee: J. A. Green Company, Trinidad, Calif.

[21] Appl. No.: 746,917

[22] Filed: Jun. 20, 1985

[51] Int. Cl.$^4$ ............................................. G01N 29/00
[52] U.S. Cl. ......................................... 73/581; 73/597
[58] Field of Search .................. 73/581, 597, 629, 761

[56] References Cited

U.S. PATENT DOCUMENTS

| | | | |
|---|---|---|---|
| 3,822,587 | 7/1974 | Makino et al. | 73/581 |
| 3,918,294 | 11/1975 | Makino et al. | 73/581 |
| 3,969,810 | 7/1976 | Pagano | 73/581 |
| 3,975,948 | 8/1976 | Makino et al. | 73/581 |
| 4,014,208 | 3/1977 | Moore et al. | 73/761 |
| 4,088,907 | 5/1978 | Jones et al. | 73/587 |
| 4,363,242 | 12/1982 | Heyman | 73/761 |

*Primary Examiner*—Stephen A. Kreitman
*Attorney, Agent, or Firm*—Townsend & Townsend

[57] ABSTRACT

A method and apparatus for measuring tensile stress in a fastener already in place. This method capitalizes on the discovery that a longitudinal wave will travel roughly twice as fast as a transverse wave and the times-of-flight of the two waves are affected to different degrees by tensile stress. Longitudinal and transverse ultrasonic signals are applied to a first end of the fastener. The longitudinal and transverse signals are detected at this same first end of the fastener after they are reflected off of the second end of the fastener. The time-of-flight for each of the longitudinal and transverse waves is measured. The tensile stress, T, in the fastener is then determined by applying substantially the following equation:

$$T = \frac{v_{10}t_1 - v_{20}t_2}{\dfrac{D_1(v_{10}t_1/2 - k)}{\lambda + 2\mu} - \dfrac{D_2(v_{20}t_2/2 - k)}{\mu}}$$

where $v_{10}$ and $v_{20}$ = the velocities of the longitudinal and transverse signals, respectively, in a similar fastener not under stress;

$k$ = the length of the unstressed portion of the fastener;

$\lambda$ and $\mu$ = Lame' constants for the fastener material; and $D_1$ and $D_2$ = material constants for the fastener representing a simplified combination of second and third order elastic material constants.

28 Claims, 4 Drawing Figures

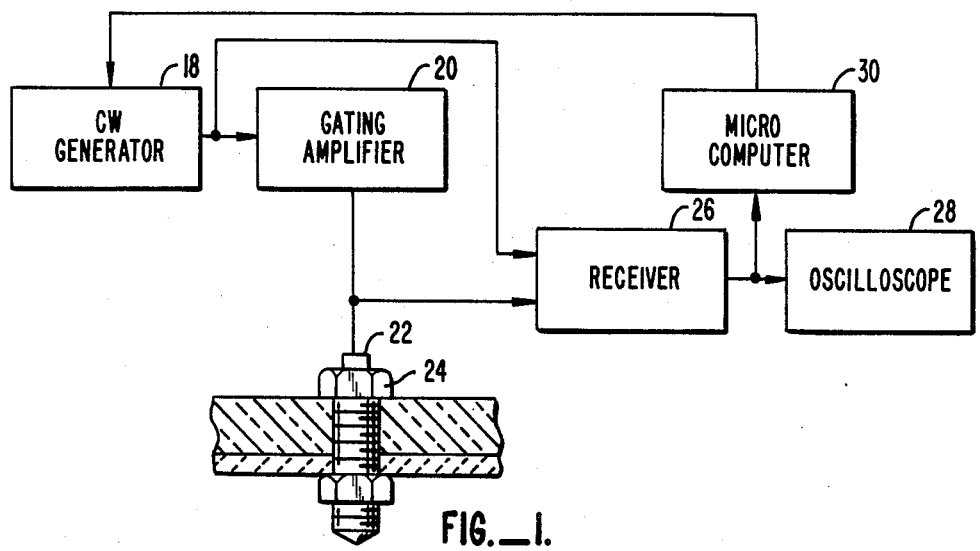
FIG._1.
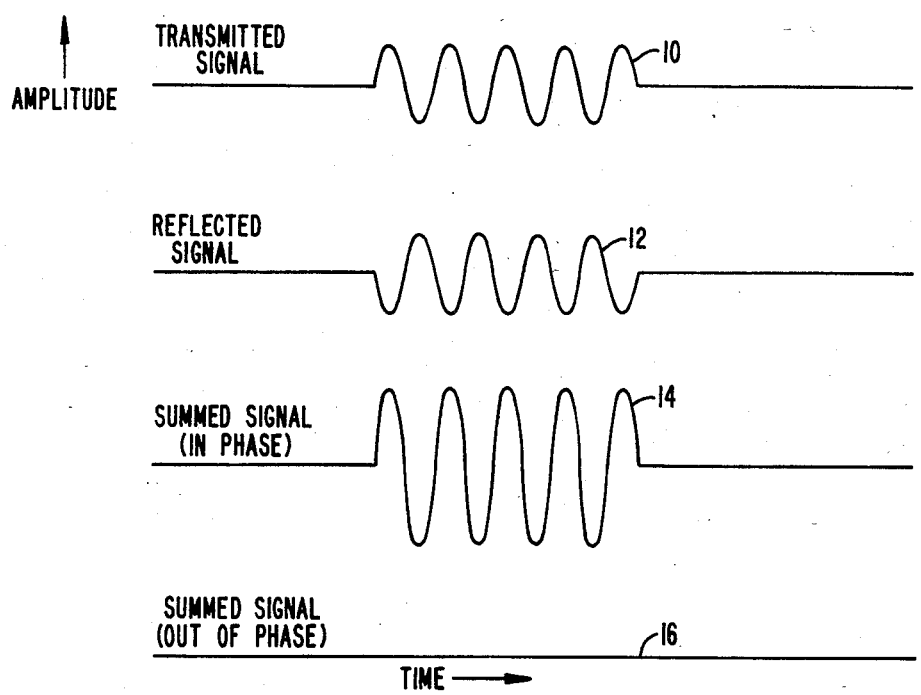
FIG._2.

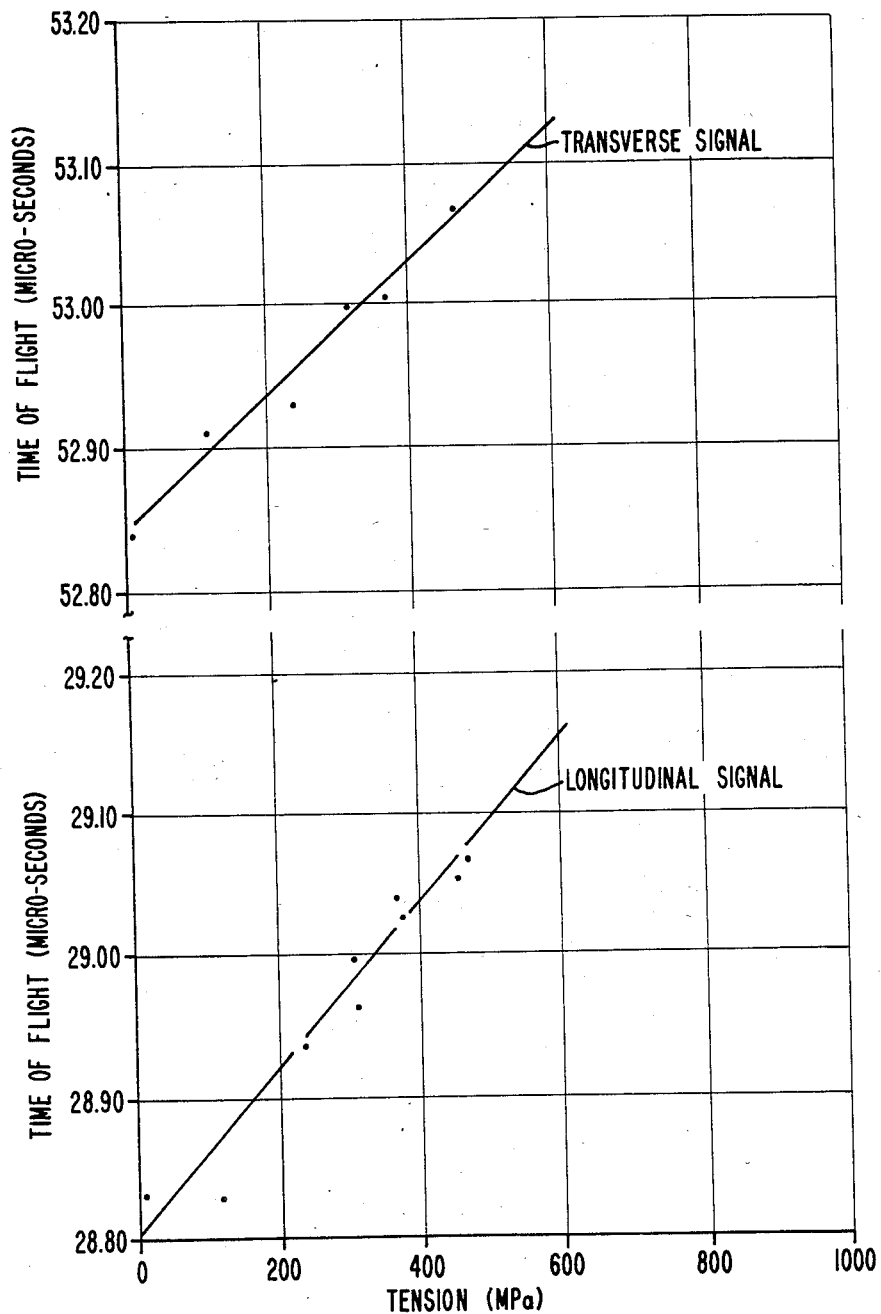
FIG._3.

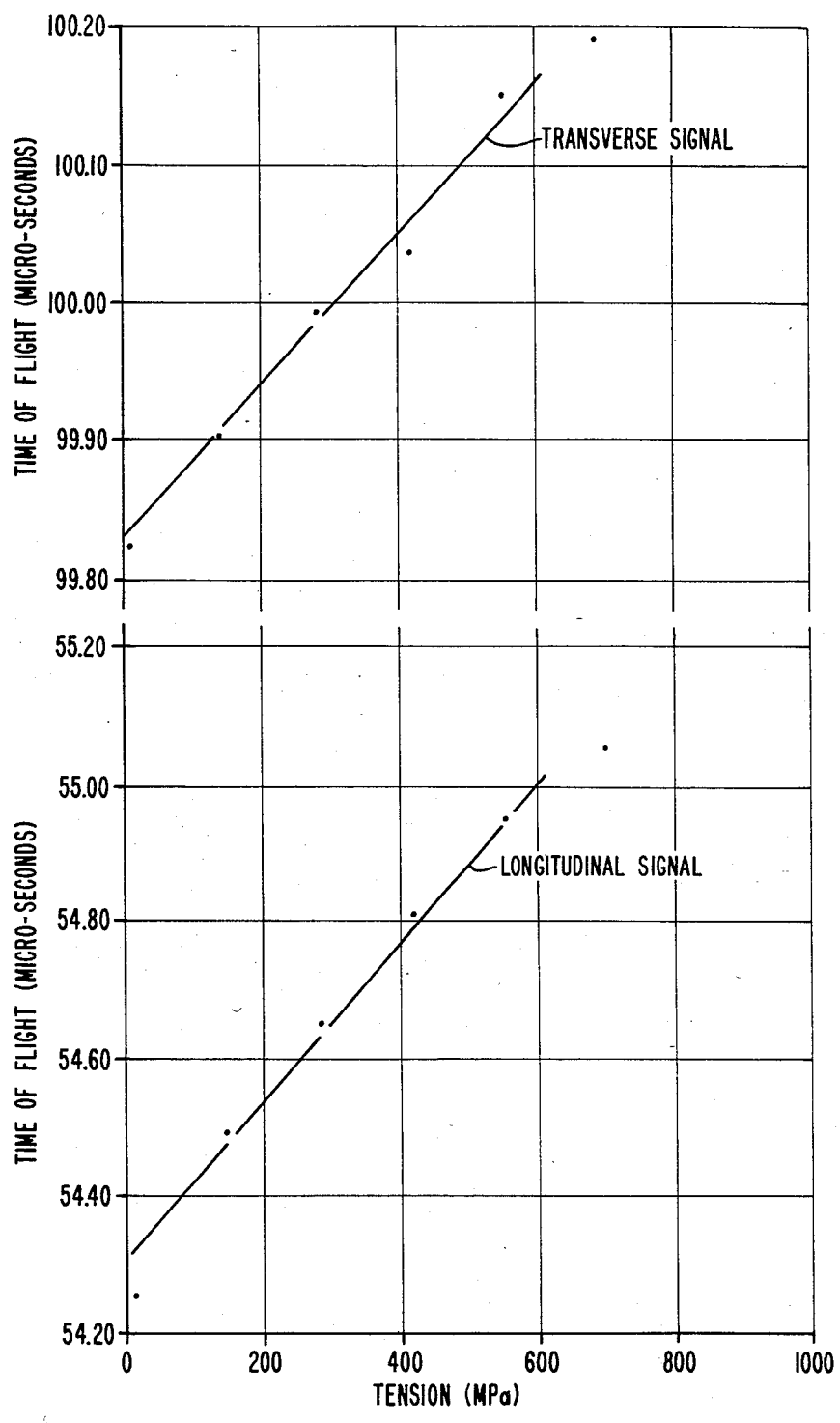
FIG._4.

METHOD FOR MEASURING FASTENER STRESS UTILIZING LONGITUDINAL AND TRANSVERSE ULTRASONIC WAVE TIME-OF-FLIGHT

BACKGROUND OF THE INVENTION

This invention relates to the measurement of stress in a fastener under tension utilizing ultrasonic signals.

There are many methods for measuring tension in a bolt or other fastener. Perhaps the most commonly known is the use of a torque wrench which measures the torque applied as the bolt is installed. This applied torque is roughly proportional to the tension. Ultrasonic signals can be used to give a more accurate measure of tension in a bolt while the bolt is being installed. U.S. Pat. No. 3,969,810 to Pagano shows a method for measuring the tension in a bolt by measuring the time-of-flight for an ultrasonic signal which is transmitted down the length of the bolt and reflected back. This time-of-flight is first measured when the bolt is not under stress and is then measured as the bolt is placed under stress, with the variation in the time-of-flight being approximately proportional to the tension.

U.S. Pat. No. 4,014,208 to Moore discloses another method for measuring tension in a bolt while it is being installed using ultrasonic signals. A pair of pulses are transmitted down a bolt before installation, and the frequency at which the second echo of the first pulse coincides with the first echo of the second pulse is noted. As the bolt is installed, the frequency is varied to maintain the coincidence of these echoes. The change in frequency is then used to calculate the tension.

It is desirable in some circumstances to measure the tension in a bolt that has already been installed without loosening and retightening the bolt. Such a method is disclosed in U.S. Pat. No. 3,975,948 to Makino. This patent shows a method for determining tensile stress in a bolt which has already been installed by using longitudinal and transverse ultrasonic waves. A longitudinal wave can be visualized as the wave produced by hitting the end of the bolt with a hammer. A transverse wave can be visualized by thinking of the bolt as a clothesline with a wave being sent down its length by moving one end rapidly up and down. A capacitor in a transmitting circuit is adjusted so that first the frequency of the longitudinal waves, and then the frequency of the transverse waves, become one of the resonant frequencies of the bolt. The tensile stress of the bolt is then calculated using the determined resonant frequencies for the longitudinal and transverse waves in accordance with a mathematical formula. The formula requires the use of a calibration curve which must be separately determined for each bolt type and each different configuration of the stressed and unstressed portions of the bolt.

Makino thus discloses a method for measuring the tension in a bolt or other fastener which is already under stress, but this is accomplished at the sacrifice of simplicity by requiring adjustments to a capacitor to determine resonant frequencies.

SUMMARY OF THE INVENTION

The present invention is a method and apparatus for measuring tensile stress in a fastener already under tension. This method capitalizes on the discovery that a longitudinal wave will travel roughly twice as fast as a transverse wave and the times-of-flight of the two waves are affected to different degrees by tensile stress. Longitudinal and transverse ultrasonic signals are applied to a first end of the fastener. The longitudinal and transverse signals are detected at this same first end of the fastener after they are reflected off of the second end of the fastener. The time-of-flight for each of the longitudinal and transverse waves is measured. The tensile stress, T, in the fastener is then determined by applying substantially the following equation:

$$T = \frac{v_{10} t_1 - v_{20} t_2}{\dfrac{D_1 (v_{10} t_1/2 - k)}{\lambda + 2\mu} - \dfrac{D_2 (v_{20} t_2/2 - k)}{\mu}} \quad (1)$$

where:

$v_{10}$ and $v_{20}$ = the velocities of the longitudinal and transverse signals, respectively, in a similar fastener not under stress;

$k$ = the length of the unstressed portion of the fastener;

$\lambda$ and $\mu$ = Lame' constants for the fastener material; and $D_1$ and $D_2$ = material constants for the fastener representing a simplified combination of second and third order elastic material constants.

The time-of-flight can be measured by any number of methods. In one embodiment, the transmitted signal is added to the detected signal and the frequency of the signal is varied until the two signals are out of phase by 180°, thereby giving destructive interference which gives a summed signal of 0. The frequency is then varied to a next adjacent frequency at which the detected and applied signals are 180° out of phase. The time-of-flight, t, can then be determined from the equation:

$$t = 1/(f_1 - f_2).$$

where $f_1$ and $f_2$ are the two adjacent frequencies at which the summed signal is a null. This calculation is carried out separately for the longitudinal and transverse (shear) signals.

Preferably, a piezoelectric crystal generates a single signal having longitudinal and transverse components. Because the longitudinal and transverse signals have different times-of-flight, they can be separately monitored at the detecting circuit even though both are generated simultaneously. The pulse length of the generated signal is long enough to enable detection and short enough to ensure that the longitudinal reflected pulse does not overlap the transverse pulse when they are detected.

A number of time measurements are made and averaged to reduce the error by giving an average time. This is done by determining twenty adjacent frequencies at which destructive interference occurs and dividing the difference between the first and last frequencies by 19.

The various constants are determined by making measurements upon fasteners of the same type under a known tensile stress. These determined values are then used to calculate the tensile stress from measurements of a fastener in which the tensile stress is not known. Thus, for example, the present invention uses one set of constants for a ¾" Grade 5 steel bolt and another set of constants for a ⅞" Grade 8 steel bolt. The present invention provides a relatively simple method of measuring tensile stress in a fastener that has already been placed under stress.

For a fuller understanding of the nature and advantages of the invention, reference should be made to the ensuing detailed description taken in conjunction with the accompanying drawings.

BRIEF DESCRIPTION OF THE DRAWINGS

FIG. 1 is a block diagram of a preferred embodiment of the measuring circuit of the present invention;

FIG. 2 is a schematic diagram of the signals used in the present invention;

FIG. 3 is a chart of experimental time of flight measurements for a $\frac{3}{4}'' \times 3''$ grade 5 steel bolt; and FIG. 4 is a chart of experimental time of flight measurements for a $\frac{7}{8}'' \times 6''$ grade 8 steel bolt.

DETAILED DESCRIPTION OF THE PREFERRED EMBODIMENT

The present invention relies on the fact that the longitudinal sound velocity, $v_1$, along the axis of a fastener will vary more strongly with applied tensile stress than the shear velocity, $v_2$. The variation of the transverse velocity is about $1\frac{1}{2}$ orders of magnitude less than the variation of the longitudinal velocity. If the variation of transverse and longitudinal sound velocities with tensile strength are known, and if one measures a round trip time-of-flight for pulses transmitted down the length of the bolt for each type of wave, then one can calculate the stress in the bolt without knowing the length of the bolt but only knowing the portion of the length of the bolt which is under stress.

A simplification of the F. D. Murnaghan equation gives the following equations:

$$\rho_0 v_1^2 = (\lambda + 2\mu) - D_1 T \tag{2}$$

and $$\rho_0 v_2^2 = \mu - D_2 T \tag{3}$$

where
$\rho_0$ = the density of the bolt material;
$\lambda$ and $\mu$ = the Lame' constants;
$D_1$ and $D_2$ = material constants;
$T$ = the tensile stress in the bolt.

The Lame' constants are elastic constants for materials and vary according to the particular material. Values of these Lame' constants for steel bolts are given in Table I of the Appendix. The constants $D_1$ and $D_2$ represent a simplification of a number of second and third order elastic constants as would be readily recognized by examination of the Murnaghan equation.

If $a$ is the (unknown) length of the bolt, then the round trip time-of-flight for a longitudinal pulse ($t_1$) and for a transverse pulse ($t_2$) will be:

$$t_1 = 2a/v_1 \tag{4}$$

and $$t_2 = 2a/v_2 \tag{5}$$

By substituting Equations (4) and (5) into Equations (2) and (3) and solving for T we obtain:

$$T = [(t_2/t_1)^2 \mu - (2+2\mu)]/[(t_2/t_1)^2 D_2 - D_1] \tag{6}$$

Since the Lame' constants are known and the constants $D_1$ and $D_2$ can be measured, we need only accurately measure the times-of-flight $t_1$ and $t_2$ to calculate the tensile stress in the bolt. However, a correction will need to be made to account for the unstressed portion of the bolt at the head and at the threads.

Since only a portion of the bolt will be under stress, the total length of the bolt, L, can be represented by the following equation:

$$L = k + a \tag{7}$$

where
$k$ = the unstressed portion of the bolt; and
$a$ = the portion of the bolt under stress.

The time-of-flight for longitudinal and transverse waves propagated down the length of the bolt and reflected from the far end will be:

$$t_1 = 2(a/v_1 + k/v_{10}) \tag{8}$$

and $$t_2 = 2(a/v_2 + k/v_{20}) \tag{9}$$

where $v_1$ and $v_2$ are the sound velocities in the presence of the stress, $v_{10}$ and $v_{10}$ are the sound velocities in the unstressed material, and the subscripts 1 and 2 refer to longitudinal and transverse waves, respectively. To the first order in T, the expressions for $v_1$ and $v_2$ given in equations (2) and (3) can be rewritten to give:

$$v_1 = v_{10}[1 - D_1 T/2(\lambda + 2\mu)]; \tag{10}$$

and $$v_2 = v_{20}[1 - D_2 T/2\mu] \tag{11}$$

The relationship between the portion of the length of the bolt under stress, $a$, and its unstressed value $a_0$ will be:

$$a = a_0[1 + T/E] \tag{12}$$

where E is Young's Modulus. By putting (10) and (11) into (8) and (9) and eliminating $a$, we obtain equation (1):

$$T = \frac{v_{10} t_1 - v_{20} t_2}{\dfrac{D_1 (v_{10} t_1/2 - k)}{\lambda + 2\mu} - \dfrac{D_2 (v_{20} t_2/2 - k)}{\mu}} \tag{1}$$

The material constants $D_1$ and $D_2$ can be determined by placing a similar fastener under a known stress. The time-of-flight of the longitudinal and transverse waves is then measured for zero stress and at successively higher values of stress. Equations (10)–(12) are used in equations (8), (9) to obtain the following equations:

$$t_1 = (2/v_{10}) \left[ \frac{a_0 (1 + T/E)}{(1 - D_1 T/2 (\lambda + 2\mu))} + k \right] \tag{13}$$

$$t_2 = (2/v_{20}) \left[ \frac{a_0 (1 + T/E)}{(1 - D_2 T/2\mu)} + k \right] \tag{14}$$

The unstressed length of the fastener, $a_0 + k$, can be determined by measurement. Since $T/E << 1$, $D_1 T << (\lambda + 2\mu)$, and $D_2 T << \mu$, we can rewrite these equations to the first order in these quantities to obtain:

$$t_1 = (2/v_{10})\{a_0[1 + T(D_1/2(\lambda + 2\mu) + 1/E)] + k\} \tag{15}$$

$$t_2 = (2/v_{20})\{a_0[1 + T(D_2/2\mu + 1/E)] + k\} \quad (16)$$

The coefficients of T in these equations, which represent the slopes of the straight lines in FIGS. 4 and 5, are:

$$a_0[D_1/(\lambda+2\mu)+2/E]/v_{10} \quad (17);$$

and $$a_0[D_2/\mu+2/E]/v_{20} \quad (18)$$

Thus, given the known values of the constants for a similar fastener, the tensile stress in the fastener can be determined by simply measuring the times-of-flight for the longitudinal and transverse waves and knowing the approximate length of the unstressed portion of the fastener. Several techniques can be used to measure the round trip time-of-flight, such as pulse arrival, pulse echo overlap, phase detection, or sing-a-round. Preferably, the phase detection method is utilized because it is accurate and easier to automate.

The phase detection method can be understood by reference to FIG. 2. A transmitted longitudinal or transverse signal 10 consists of a short pulse of a sine wave. A reflected signal 12 is a corresponding pulse which has been reflected off the far end of the fastener. These two signals are added together to produce a summed signal. When transmitted signal 10 and reflected signal 12 are in phase, a higher amplitude summed signal 14 is produced. However, when transmitted signal 10 and reflected signal 12 are exactly 180° out-of-phase, one signal will cancel the other, giving a zero amplitude summed signal 16. The condition for this zero amplitude or destructive interference signal (or null) is given by:

$$mt = (n + \tfrac{1}{2})/f$$

where,
t = round trip time-of-flight;
f = ultrasonic frequency;
n = any integer; and
m = the echo that is being detected.

The transmitted signal will bounce back and forth between the two ends of the fastener giving 1st, 2nd, 3rd, etc. echoes which decrease in amplitude each time. By varying the frequency to give a sequence of m successive nulls of the summed signal, we then have the equations:

$$mt = (n + \tfrac{1}{2})/f$$

and $$mt = (m + n + \tfrac{1}{2})/f'$$

where f and f' are the first and last frequencies giving nulls.

By subtracting these equations, we obtain the single equation:

$$mt(f'-f) = n$$

or $$t = 1/(f'-f)$$

This equation can thus be used to calculate the desired pulse time-of-flight. The accuracy of the value can be improved by measuring a large number of successive frequencies and determining the average time-of-flight. The frequency need not be recorded except for the first and last frequencies and the resultant frequency difference can be divided by the number of nulls detected less one. These measurements are made independently for the longitudinal and transverse waves. The two times-of-flight thus determined for the longitudinal and transverse waves are plugged into equation (1) to give the tensile stress.

A measuring circuit according to the present invention is shown in FIG. 1. A continuous wave generator 18 produces a high frequency signal, preferably 5-10 megahertz. The signal from CW generator 18 is applied to a gating amplifier 20. Amplifier 20 amplifies the signal and gates it to give pulses of 1-5 microseconds duration. These pulses are applied by an ultrasonic transducer 22 to a first end of a bolt 24. The reflected pulse is detected by transducer 22 and applied to receiver 26. Receiver 26 also receives the transmitted signal from CW generator 18. These signals are summed in receiver 26 and applied to an oscilloscope 28.

By adjusting the frequency of CW generator 18 until a sequence of nulls are observed on oscilloscope 28, the times-of-flight can be determined as noted earlier. The measurements can either be made manually using oscilloscope 28 or automatically using a microcomputer 30 coupled to receiver 26 and CW generator 18. Microcomputer 30 is programmed with the various required constants and causes a variation of frequencies from CW generator 18 to continue until the desired count of nulls from receiver 26 is detected.

FIG. 3 shows actual experimentally measured round trip time-of-flight data for a longitudinal and transverse wave in a $\tfrac{3}{4}'' \times 3''$ Grade 5 steel bolt as a function of applied tensile stress. This chart shows the difference in time-of-flight for transverse and longitudinal signals and the linearity of the data over a range of tensions. A similar chart is shown in FIG. 4 for longitudinal and shear waves in a $\tfrac{7}{8}'' \times 6''$ Grade 8 steel bolt. Table II in the appendix hereto gives the data points for the chart of FIG. 4.

As can be seen by reference to FIG. 1, the transmitted signal received by receiver 26 has a different path length from that of the reflected signal from ultrasonic transducer 22. Accordingly, an adjustment must be made either manually or programmed into microcomputer 30 to correct for the fact that the transmitted signal has a longer path to travel through the wires and gating amplifier 20. It is, of course, desired to compare only the paths down the bolt and back, and not the paths in other circuitry. A method for making such correction is described in an article by Peterson, G. L., Chick, B., and Junker, W., entitled "1975 Ultrasonic Symposium Proceedings," IEEE, Cat. No. 75, CHO 994-4SU.

Preferably, an ultrasonic transducer 22 is used which produces a signal having both transverse and longitudinal components. Due to the fact that the longitudinal wave travels approximately twice as fast as the transverse (shear) wave, the reflected waves can be separately identified and measured. The longitudinal wave can be envisioned as hitting the end of the bolt with a hammer and the transverse or shear wave can be envisioned as a wave going down the length of the bolt similar to a wave along a clothesline generated by moving one end of the clothesline up and down. Preferably, a 5-10 megahertz signal is used and gated for a pulse of 1-5 microseconds to give 20-100 cycles. This should give a pulse which is short enough so that successive echoes do not overlap and long enough to enable detection. The pulsing can be done every 0.1-0.5 milliseconds.

Ultrasonic transducer 22 preferably focuses the transmitted signals so that they reflect only from a small center portion of the far end of the bolt. Without focusing, errors can arise where the end of the bolt is rounded and the signal will have a different distance to travel depending upon which portion of the far end of the bolt it reflects from.

As will be understood by those familiar with the art, the present invention may be embodied in other specific forms without departing from the spirit or essential characteristics thereof. For example, the material constants $D_1$ and $D_2$ could be expanded to provide a more complicated equation. Or, another method rather than phase detection could be used for measuring the time-of-flight of the ultrasonic signal. Accordingly, the disclosure of the preferred embodiment of the present invention is intended to be illustrative, but not limiting of the scope of the invention which is set forth in the following claims.

APPENDIX

TABLE 1

Material Constants Required For The Calculation Of Tensile Stress From Ultrasonic Measurements

| | Grade 5 Bolts | | Grade 8 Bolts | | ARMCO IRON |
|---|---|---|---|---|---|
| | $\frac{3}{4}''$ | $\frac{7}{8}''$ | $\frac{3}{4}''$ | $\frac{7}{8}''$ | |
| $D_1$ | 9.65 | 8.94 | 11.92 | 9.17 | 14.70 |
| $D_2$ | 0.73 | 0.39 | 0.50 | 0.38 | −0.22 |
| $v_1$ (cm/μsec) | 0.5914 | 0.5912 | 0.5917 | 0.5916 | 0.5922 |
| $v_2$ (cm/μsec) | 0.3230 | 0.3235 | 0.3224 | 0.3229 | 0.3241 |
| k (cm) | 1.5 | 1.75 | 1.5 | 1.75 | |
| $\lambda + 2\mu$ (GPa) | 276. | 276. | 276. | 276. | |
| $\mu$ (GPa) | 83. | 83. | 83. | 83. | |

The values for Armco Iron are from the paper by Hughes and Kelly, Phys. Rev. 92, 1145 (1953).

TABLE 2

Ultrasonic Determination Of Stress In A $\frac{7}{8}'' \times 6''$ Grade 8 Steel Bolt

| Applied Tensile Stress (MPa) | $t_1$ (μsec) | $t_2$ (μsec) | Calculated Stress (MPa) | % Error |
|---|---|---|---|---|
| 684 | 55.251 | 100.407 | 640. | −6 |
| 545 | 55.155 | 100.368 | 540. | −1 |
| 410 | 55.016 | 100.312 | 380 | −7 |
| 269 | 54.889 | 100.256 | 240 | −11 |
| 0 | 54.639 | 100.122 | −10 | |

What is claimed is:

1. A method for measuring tensile stress in a fastener under tensile stress comprising:
    applying a longitudinal ultrasonic signal to a first end of said fastener;
    applying a transverse ultrasonic signal to said first end of said fastener;
    detecting said longitudinal and transverse signals at said first end after reflection from a second end of said fastener;
    measuring the time-of-flight, $t_1$, taken by said longitudinal signal to travel from said first end to said second end and back;
    measuring the time-of-flight, $t_2$, for said transverse signal to travel from said first end to said second end and back; and
    determining the tensile stress, T, in said fastener substantially according to the equation $$T = \frac{v_{10}t_1 - v_{20}t_2}{\frac{D_1(v_{10}t_1/2 - k)}{\lambda + 2\mu} - \frac{D_2(v_{20}t_2/2 - k)}{\mu}}$$

(where $v_{10}$ and $v_{20}$ = velocities of said longitudinal and transverse signals, respectively, in said fastener without stress, k = unstressed length of said fastener, $\lambda$ and $\mu$ = the Lame' constants for said fastener and $D_1$ and $D_2$ represent elastic properties of said fastener).

2. The method of claim 1 wherein said steps of measuring times $t_1$ and $t_2$ each comprise the steps of: determining a frequency $f_1$ where said detected signal is out of phase with said applied signal by approximately 180°;
    determining a second frequency $f_2$ of said signal, $f_2$ being the next adjacent frequency at which said detected signal is out of phase with said applied signal by approximately 180°; and
    determining the time-of-flight from the frequency difference according to the equation $t = 1/(f_1 - f_2)$.

3. The method of claim 2 wherein said steps of determining frequencies $f_1$ and $f_2$ each comprise the steps of:
    adding said applied signal to said detected signal after reflection; and
    varying the frequency of said signal until the sum of said applied and detected signals is approximately zero.

4. The method of claim 2 further comprising the step of averaging a plurality of frequency difference determinations.

5. The method of claim 1 wherein said signals are sinusoidal with a frequency of 5-10 mHz and further comprising the step of gating said signals to produce pulses of 1 to 5 microseconds duration.

6. The method of claim 5 further comprising the steps of:
    generating said sinusoidal signals; and
    amplifying said sinusoidal signals.

7. The method of claim 6 further comprising the step of compensating for the difference in paths travelled by said applied and said detected signals outside said fastener.

8. The method of claim 1 further comprising the step of conditioning said first end of said fastener to give a flat surface for applying and detecting said signals.

9. The method of claim 1 further comprising the step of focusing said signals so that they are reflected from a center portion of said second end of said fastener.

10. The method of claim 1 wherein said longitudinal and transverse signals are simultaneously applied to said first end of said fastener.

11. A method for measuring tensile stress in a fastener comprising:
    simultaneously applying a pulse of a longitudinal ultrasonic sinusoidal signal and a transverse ultrasonic sinusoidal signal to said first end of said fastener;
    detecting said longitudinal and transverse signals at said first end after reflection from a second end of said fastener;

adding said applied signal to said detected signal for each of said longitudinal and transverse signals to produce a summed signal;

varying the frequency of said sine wave signal for each of said longitudinal and transverse signals to a frequency f(1), where said longitudinal summed signal is approximately zero, and a frequency of f(t), where said transverse signal is approximately zero;

varying said frequency to next adjacent frequencies $f(1)_2$ and $f(t)_2$ where said longitudinal and transverse summed signals, respectively, are approximately zero;

determining the times-of-flight, $t_1$ and $t_2$, for said longitudinal and transverse signals, respectively, to travel the length of said fastener and back from the frequency difference according to the equation $t = 1/(f_1 - f_2)$;

determining the tensile stress in said fastener substantially according to the equation $$T = \frac{v_{10}t_1 - v_{20}t_2}{\frac{D_1(v_{10}t_1/2 - k)}{\lambda + 2\mu} - \frac{D_2(v_{20}t_2/2 - k)}{\mu}}$$

(where $v_{10}$ and $v_{20}$ = velocities of said longitudinal and transverse signals, respectively, in said fastener without stress, k = unstressed length of said fastener, $\lambda$ and $\mu$ = the Lame' constants for said fastener and $D_1$ and $D_2$ represent elastic properties of said fastener).

12. The method of claim 11 further comprising the step of averaging a plurality of frequency difference determinations.

13. The method of claim 11 wherein said signals are sinusoidal with a frequency of 5-10 mHz and further comprising the step of gating said signals to produce pulses of 1 to 5 microseconds duration.

14. The method of claim 11 further comprising the steps of:

generating said sinusoidal signals; and amplifying said sinusoidal signals.

15. The method of claim 11 further comprising the step of compensating for the difference in paths travelled by said applied and said detected signals outside said fastener.

16. The method of claim 11 further comprising the step of conditioning said first end of said fastener to give a flat surface for applying and detecting said signals.

17. The method of claim 11 further comprising the step of focusing said signals so that they are reflected from a center portion of said second end of said fastener.

18. A method for measuring tensile stress in a fastener comprising:

applying a longitudinal ultrasonic signal to a first end of said fastener;

applying a transverse ultrasonic signal to said first end of said fastener;

detecting said longitudinal and transverse signals at said first end after reflection from a second end of said fastener;

measuring the time, $t_1$, taken by said longitudinal signal to travel from said first end to said second end and back;

measuring the time, $t_2$, for said transverse signal to travel from said first end to said second end and back;

measuring the length, k, of the unstressed portion of the fastener;

determining the velocities, $v_{10}$ and $v_{20}$, of said longitudinal and transverse signals, respectively, in a similar fastener not under stress;

determining the material constants, $D_1$ and $D_2$, for said similar fastener under a known tensile stress T from the equations $$t_1 = (2/v_{10})\left[\frac{a_0(1 + T/E)}{(1 - D_1 T/2 (\lambda + 2\mu))} + k\right]$$

and $$t_2 = (2/v_{20})\left[\frac{a_0(1 + T/E)}{(1 - D_2 T/2\mu)} + k\right]$$

(wherein $a_0$ equals the unstressed length of a portion of said similar fastener to be put under stress, E equals Young's Modulus, $\lambda$ and $\mu$ are the Lame' constants for the fastener); and determining the tensile stress, T, from the equation $$T = \frac{v_{10} t_1 - v_{20} t_2}{\frac{D_1 (v_{10} t_1/2 - k)}{\lambda + 2\mu} - \frac{D_2 (v_{20} t_2/2 - k)}{\mu}} \quad (1)$$

19. An apparatus for measuring tensile stress in a fastener comprising:

means for applying a longitudinal ultrasonic signal to a first end of said fastener;

means for applying a transverse ultrasonic signal to said first end of said fastener;

means for detecting said longitudinal and transverse signals at said first end after reflection from a second end of said fastener;

means for measuring the time-of-flight, $t_1$, taken by said longitudinal signal to travel from said first end to said second end and back;

means for measuring the time-of-flight, $t_2$, for said transverse signal to travel from said first end to said second end and back; and means for determining the tensile stress, T, in said fastener substantially according to the equation $$T = \frac{v_{10}t_1 - v_{20}t_2}{\frac{D_1(v_{10}t_1/2 - k)}{\lambda + 2\mu} - \frac{D_2(v_{20}t_2/2 - k)}{\mu}}$$

(where $v_{10}$ and $v_{20}$ equal velocities of said longitudinal and transverse signals, respectively, in said fastener without stress, k equals the unstressed length of said fastener, $\lambda$ and $\mu$ are the Lame' constants for said fastener and $D_1$ and $D_2$ represent elastic properties of said fastener).

20. The apparatus of claim 19 wherein said means for measuring times $t_1$ and $t_2$ each comprise:

means for determining a frequency $f_1$ where said detected signal is out of phase with said applied signal by approximately 180°;

means for determining a second frequency $f_2$ of said signal, $f_2$ being the next adjacent frequency at which said detected signal is out of phase with said applied signal by approximately 180°; and means for determining the time-of-flight from the frequency difference according to the equation $t = 1/(f_1 - f_2)$.

21. The apparatus of claim 20 wherein said means for determining frequencies $f_1$ and $f_2$ each comprise:

means for adding said applied signal to said detected signal after reflection; and means for varying the frequency of said signal until the sum of said applied and detected signals is approximately zero.

22. The apparatus of claim 20 further comprising means for averaging a plurality of frequency difference determinations.

23. The apparatus of claim 19 wherein said signals are sinusoidal with a frequency of 5–10 mHz and further comprising means for gating said signals to produce pulses of 1 to 5 microseconds duration.

24. The apparatus of claim 23 further comprising:
means for generating said sinusoidal signals; and
means for amplifying said sinusoidal signals.

25. The apparatus of claim 24 further comprising means for compensating for the difference in paths travelled by said applied and said detected signals outside said fastener.

26. The apparatus of claim 19 further comprising means for conditioning said first end of said fastener to give a flat surface for applying and detecting said signals.

27. The apparatus of claim 19 further comprising means for focusing said signals so that they are reflected from a center portion of said second end of said fastener.

28. The apparatus of claim 19 further comprising means for applying said longitudinal and transverse signals to said first end of said fastener.

* * * * *